United States Patent
Bielmeier et al.

(10) Patent No.: US 10,101,415 B2
(45) Date of Patent: Oct. 16, 2018

(54) OPERATION OF A MAGNETIC RESONANCE APPARATUS TAKING INTO ACCOUNT PERSONS FITTED WITH IMPLANTS

(71) Applicants: Wolfgang Bielmeier, Erlangen (DE); Gerhard Brinker, Erlangen (DE); Nikolaus Demharter, Dormitz (DE); Bernd Erbe, Erlangen (DE); Matthias Gebhardt, Erlangen (DE); Jürgen Nistler, Erlangen (DE); Dominik Paul, Bubenreuth (DE); Carsten Prinz, Baiersdorf (DE); Gudrun Ruyters, Erlangen (DE); Stephan Stöcker, Baiersdorf (DE); Markus Vester, Nürnberg (DE); Swen Campagna, Engelthal (DE)

(72) Inventors: Wolfgang Bielmeier, Erlangen (DE); Gerhard Brinker, Erlangen (DE); Nikolaus Demharter, Dormitz (DE); Bernd Erbe, Erlangen (DE); Matthias Gebhardt, Erlangen (DE); Jürgen Nistler, Erlangen (DE); Dominik Paul, Bubenreuth (DE); Carsten Prinz, Baiersdorf (DE); Gudrun Ruyters, Erlangen (DE); Stephan Stöcker, Baiersdorf (DE); Markus Vester, Nürnberg (DE); Swen Campagna, Engelthal (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 15/488,478

(22) Filed: Apr. 15, 2017

(65) Prior Publication Data
US 2017/0299667 A1 Oct. 19, 2017

(30) Foreign Application Priority Data
Apr. 15, 2016 (DE) ........................ 10 2016 206 398

(51) Int. Cl.
*G01V 3/00* (2006.01)
*G01R 33/28* (2006.01)
(Continued)

(52) U.S. Cl.
CPC ............ *G01R 33/288* (2013.01); *A61B 5/055* (2013.01); *G01R 33/543* (2013.01)

(58) Field of Classification Search
CPC .................................................... G01R 33/288
(Continued)

(56) References Cited

U.S. PATENT DOCUMENTS 7,561,915 B1    7/2009  Cooke et al.
9,037,258 B2 *  5/2015  Johnson ................... A61N 1/08
                                                    607/63

(Continued)

FOREIGN PATENT DOCUMENTS

DE    102006016043 A1    10/2007
DE    202008018452U1 U1  6/2014
DE    102015216323 A1    3/2017

OTHER PUBLICATIONS

German Office Action for German Application No. 10 2016 206 398.7, dated Dec. 21, 2016, with English Translation.
(Continued)

*Primary Examiner* — Louis Arana
(74) *Attorney, Agent, or Firm* — Lempia Summerfield Katz LLC

(57) ABSTRACT

A method for operating a magnetic resonance apparatus by a safety unit, taking into account persons fitted with an implant, a safety unit, a safety system, a magnetic resonance apparatus, and a computer program product are provided. The magnetic resonance apparatus includes a first part and a second part. The first part is operated separately from the second part and includes the safety unit. During an examination of a person fitted with an implant, the safety unit checks that the magnetic resonance apparatus, in a restricted operating mode, is complying with implant-conformant limit values.

30 Claims, 6 Drawing Sheets

(51) Int. Cl.
*A61B 5/055* (2006.01)
*G01R 33/54* (2006.01)

(58) Field of Classification Search
USPC .................................................. 324/318, 322
See application file for complete search history.

(56) References Cited

U.S. PATENT DOCUMENTS

| | | |
|---|---|---|
| 9,205,268 B2* | 12/2015 | Yoon ..................... A61N 1/3718 |
| 2007/0265685 A1 | 11/2007 | Zeijlemaker |
| 2010/0312091 A1 | 12/2010 | Krueger et al. |
| 2012/0086449 A1 | 4/2012 | Graesslin et al. |
| 2014/0303485 A1* | 10/2014 | Weiss ................... G01R 33/288 |
| | | 600/411 |
| 2017/0059670 A1 | 3/2017 | Gebhardt et al. |

OTHER PUBLICATIONS

ICEI IEC 62304; Nternational Standard, First edition; May 2006; "Medical device software—Software life cycle processes" Reference No. CEI/IEC 62304:2006.
Norme Internationale IEC 60601-2-33 with amendement 2; 2010.
Norme Internationale IEC 60601-2-33, Edition 3.0; 2010.
Supplemental German Office Action for German Application No. 102016206398.7 dated Feb. 7, 2017.
European Search Report for corresponding Application No. 17158047. 5-1568, dated Nov. 20, 2017.

* cited by examiner

OPERATION OF A MAGNETIC RESONANCE APPARATUS TAKING INTO ACCOUNT PERSONS FITTED WITH IMPLANTS

This application claims the benefit of DE 10 2016 206 398.7, filed on Apr. 15, 2016, which is hereby incorporated by reference in its entirety.

BACKGROUND

The present embodiments relate to operating a magnetic resonance apparatus using a safety unit, taking into account persons fitted with implants.

During a magnetic resonance examination, i.e. when Magnetic Resonance Imaging (MRI) is being carried out, for acquisition of magnetic resonance signals by a magnetic resonance apparatus, electromagnetic fields, in particular gradient fields and radio-frequency fields, will usually be employed in accordance with a measurement protocol. To create the gradient fields the magnetic resonance apparatus usually has a gradient coil unit with at least one gradient coil. The magnetic resonance apparatus further mostly has a radio-frequency antenna unit, with which radio-frequency fields can be created for excitation of atomic nuclei.

The gradient fields can cause peripheral nerve stimulations (PNS) and the radio-frequency fields can cause heating. Therefore standardization bodies, such as e.g. IEC 60601-2-33, demand that these PNS and/or heatings will be monitored and restricted. In the past patients fitted with implants were as a rule excluded from a magnetic resonance examination. The development of new, to some extent MR-compatible implants, which can be characterized in accordance with Standard IEC 60601-2-33 by "Fixed Parameter Option: Basic" (FPO:B) makes it possible to allow magnetic resonance examination for persons fitted with implants if specific conditions will be fulfilled.

Typical implants that are to some extent MR-compatible can for example be heart pacemakers, defibrillators and further implants, such as might be used for administration of medication or for deep brain simulation or for stimulation of the spinal column. In an examination of a person fitted with such an implant when applying Standard IEC 60601-2-33, it is to be insured that the magnetic resonance apparatus will be operated in a safe operating mode, in order not to endanger the health of the person fitted with an implant. Usually a condition of the safe operating mode is that there is a restriction of the performance of the magnetic resonance apparatus, so that the safe operating mode can also be referred to as a restricted operating mode. Thus, in accordance with Standard IEC 60601-2-33 in particular, an effective $B_1^+$ value $B_1^+{}_{rms}$, a maximum $B_1^+$ value $B_1^+{}_{peak}$, an amount of an effective rate of change of a B value $(|dB/dt|_{rms})_{FPO}$ and an amount of a maximum rate of change $(|dB/dt|_{peak})_{FPO}$ may not be exceeded.

SUMMARY AND DESCRIPTION

The scope of the present invention is defined solely by the appended claims and is not affected to any degree by the statements within this summary.

The present embodiments may obviate one or more of the drawbacks or limitations in the related art. For example, a safe operation of a magnetic resonance apparatus, taking into account persons fitted with implants, is provided. For example, the requirements of Standard IEC 60601-2-33 are to be fulfilled.

Accordingly a method for operating a magnetic resonance apparatus by a safety unit, taking into account a person fitted with an implant, is proposed. In this method the magnetic resonance apparatus comprises a first part and a second part, wherein the first part will be operated separately from the second part and comprises the safety unit. During an examination of a person fitted with an implant the safety unit checks that the magnetic resonance apparatus, in a restricted operating mode, is complying with implant-conformant limit values.

The implant-conformant limit values can be predetermined for example by Standard IEC 60601-2-33, e.g. Edition 3.2. 2015-06. This makes provision in particular for the following limit values to be complied with: $B_1^+{}_{peak} \leq 30$ μT, $B_1^+{}_{rms} \leq 3.2$ μT, $(|dB/dt \oplus_{peak})_{FPO} \leq 100$ T/s $(|dB/dt|_{rms})_{FPO} \leq 56$ T/s.

The person fitted with an implant is preferably a patient having an implant that is at least to some extent MR-compatible, which is characterized as "FPO:B" for example.

The separate operation of first and second part can in particular mean that the second part does not possess any influence on one or more, preferably on all, safety-relevant functions of the first part. The separate operation of first and second part thus does not exclude the first and second part interacting with one another. In addition the separate operation of first and second part can mean in particular that, although the second part possesses influence on one or more safety-relevant functions of the first part, the first part has a mechanism, which in the event of a safety-relevant influencing of the first part by the second part, prevents any endangering of and/or injury to the person under examination fitted with an implant.

Preferably the first and the second part each have at least one self-contained processor and/or a self-contained operating system, which can be executed for example on the at least one self-contained processor. Preferably the safety unit has one or more processors, which will be operated independently of any processors of the second part.

Preferably the first part fulfills higher safety requirements than the second part. Since the examination of a person fitted with an implant will preferably be checked by the safety unit, which is included in the first part, it is especially advantageous for the first part to be embodied according to especially high safety criteria, in order to keep the risk of an examination-related injury to the person fitted with an implant as low as possible.

One form of embodiment of the method makes provision for the first part to be operated with program means, in particular software, in accordance with a first safety category and for the second part to be operated with program means, in particular software, in accordance with a second safety category, wherein the first safety category has higher safety requirements than the second safety category.

Preferably the first safety category fulfills the safety class C and the second safety category the safety classes A and/or B of Standard IEC 62304. The safety class C usually envisions specific design requirements, such as for example a proof that a predetermined architecture is correctly implemented, a description of the functionality, of the interfaces between hardware and software and/or of the flow of data to other components.

Furthermore the safety class C usually envisions specific implementation requirements, such as for example that the separation between components will be defined and their effectiveness will be verified. Furthermore one or more of the following aspects will advantageously be taken into account, documented and tested: Flow of data and flow of control, planned allocation of resources, error handling, initialization for variables to be clarified, for self-diagnosis to be taken into account, memory management and memory overflow, boundary conditions for the execution.

The use of a separately operated safety unit makes it easier to fulfill the requirements for the software in accordance with safety class C, for example in respect of resource sharing, of a central processing unit (CPU) for example and/or of random-access memory (RAM). The separation of the first and second part allows the overall system to be manufactured more easily, since preferably only the first part fulfills the increased safety requirements in accordance with safety class C, while it can also be sufficient for the second part to fulfill a lower safety class.

Advantageously signals are created and/or transmitted within the first part (e.g., by hardware). This enables requirements of safety class C to be fulfilled.

Furthermore it is conceivable for the safety requirements for the program means of the first part to be reduced entirely or partly from safety class C to safety class B, in that a safety-safeguarding concept is implemented as hardware and the program means merely monitors and/or supports the hardware functions.

One form of embodiment of the method makes provision for the first part to comprise a switching unit. Preferably the safety unit will be provided with switching information from a number of possible items of switching information by the switching unit. In this case, depending on the switching information provided, an operating mode is set from a number of possible operating modes by the safety unit.

The setting of the operating mode in this case is preferably explicitly safety-oriented, i.e. an unintentional activation of the restricted operating mode does not lead to any safety risks for the patient, but in any event reduces the availability of the magnetic resonance apparatus, since possibly all measurement protocols that would otherwise be able to be executed will no longer be able to be used. On the other hand an unintentional deactivation of the restricted operating mode is to be avoided when a restricted operating mode is necessary for safety reasons.

The switching unit can be a unit with which a desired operating mode of the magnetic resonance apparatus can be specified, in particular whether an examination is to be carried out in the restricted operating mode.

The switching information and/or the patient information is preferably provided with the aid or a signal, in particular an electronic and/or electrical signal. In particular the switching information is provided with the aid of a hardware connection, in order to guarantee a high level of safety.

In particular the switching unit can comprise a switch and/or a pushbutton.

A switch usually has either an open or a closed switching state at a particular point in time. For example, in a closed switching state a circuit is closed and in an open switching state it is interrupted. Switching information of a switch can for example be its switching state at a specific point in time and/or a change of a switching state, in particular from an open to a closed state or from a closed state to an open state.

The switching information of a pushbutton can be a switching pulse for example, which will be initiated by an actuation of the pushbutton. For example a circuit can be closed or interrupted by actuation of a pushbutton.

The provision of the switching information can be triggered by an operator of the magnetic resonance apparatus by actuation of the switching unit, for example by said operator moving a switch and/or pressing a pushbutton.

One form of embodiment of the method makes provision for the second part to comprise a patient registration unit, wherein the safety unit will be provided with patient registration information by the patient registration unit, wherein a switch of operating mode will be at least partly triggered by the patient registration information provided.

With the aid of the patient registration information the patient registration unit preferably forwards information about a change of patient to the safety unit.

If for example a previous patient has left the magnetic resonance apparatus and the examination of a subsequent patient is impending, the patient registration unit sends the patient registration information to the safety unit. In other words the patient registration information signals to the safety unit that a new patient is to be examined from now on.

Preferably the patient registration information causes an evaluation of the switching information provided, i.e. it serves as a trigger signal for such an evaluation. Depending on the result of this evaluation, the operating mode is preferably set from the number of possible operating modes. The setting of the operating mode can in particular comprise a current operating mode being retained and/or the current operating mode being changed, i.e. another of the number of possible operating modes being set.

Through account being taken of the switching information triggered by the patient registration information the probability is increased that a suitable, in particular sufficiently safe, operating mode will be set. In this way the risk can be reduced of any malfunction of the second part, which possibly fulfills lower safety requirements than the first part, leading to unsafe operation of the magnetic resonance apparatus.

One form of embodiment of the method makes provision for the number of possible operating modes to comprise an unrestricted operating mode and the restricted operating mode and for the number of possible items of switching information to comprise active switching information and passive switching information. In this form of embodiment the unrestricted operating mode is set, if at the time that the patient registration information is provided, the switching information provided is the passive switching information.

Preferably for example it is not already sufficient for a change from the restricted operating state into the unrestricted operating state for the operator to actuate the switching unit, so that the passive switching information will be provided, but above and beyond this a transmission of the patient registration information to the safety unit is necessary as a trigger signal.

Usually an unrestricted operating mode is to be understood as an operating mode in which no account will be taken of any possible implants, i.e. no attention will be paid to requirements in accordance with FPO:B.

Active switching information can be understood here as information in accordance with which an examination in the restricted operating mode is desired. By contrast passive switching information can be understood as information in accordance with which an examination in the unrestricted operating mode is desired.

A variant of the method makes provision for the restricted operating mode to be set if, at the time that the patient registration information is provided, the switching information provided is active switching information. A possible change from the unrestricted operating mode into the restricted operating mode accordingly only takes place when patient registration information is also received from the safety unit. A change into the restricted operating mode is thus made in accordance with this variant in a similar manner to a change into the unrestricted operating mode, namely on provision of patient registration information.

An alternate variant makes provision for the restricted operating mode to be set when the switching information provided is active switching information, i.e. in particular independent of any patient registration information. This provides that an activation of the restricted operating mode is possible at any time, but a deactivation is only possible on provision of the patient registration information.

Preferably the first part comprises a display unit, which displays the operating mode. Preferably the display unit comprises a visual display, such as for example a light emitting diode (LED). When the restricted operating mode is active for example, the LED lights, otherwise it does not. This makes convenient operation and monitoring of the safety unit possible, since the operating personnel can inform themselves quickly and easily about the current operating state and where necessary can react to said state. Preferably the display unit is controlled with the aid of a hardware connection.

One form of embodiment of the method makes provision for the safety unit to be provided with safety measurement data during the examination, on the basis of which the check for compliance with the implant-conformant limit values is made.

The safety measurement data can be data about currents and/or voltages of the radio-frequency antenna unit for example, for example voltages at radio-frequency coil terminals. In particular it can comprise data about wideband and/or narrowband radio-frequency excitation signals, which will be sent out by a radio-frequency antenna unit of the magnetic resonance apparatus during the examination.

In addition the safety measurement data can comprise currents and/or voltages of a gradient coil unit, in particular gradient currents, which will be applied in particular for creating gradient fields in one or more gradient coils.

Advantageously the safety measurement data is suitable for deriving safety-relevant variables, e.g. $B_1^+{}_{peak}$, $B_1^+{}_{rms}$, $(|dB/dt|_{peak})_{FPO}$ and/or $(|dB/dt|_{rms})$ therefrom, which will be produced by the magnetic resonance apparatus and compliance with which will be checked by the safety unit. However, it is also conceivable for the magnetic resonance apparatus to comprise dedicated measurement apparatuses, such as pick coils for example, through which the safety-relevant variables, in particular fields, can be at least partly directly acquired as safety measurement data.

Preferably the safety measurement data provided will be at least partly verified, in order to insure that the safety measurement data has been correctly detected and transmitted. One or more redundant measurement units is provided for verification of the measurement data for example, with which in particular redundant safety measurement data can be acquired, with which a part or all safety measurement data acquired will be compared. Moreover it is conceivable for one or more measurement units to be provided for cyclic checking of the main measurement units.

Any safety algorithms provided can thus be prevented from failing. For example a wideband comparison and/or narrowband comparison, in particular at runtime, can be carried out.

Moreover it is conceivable for a cyclic redundancy check (CRC) to be carried out, in order to check whether the safety measurement data has been transmitted correctly. This is in particular advantageous if the transmission of the safety measurement data contains software.

A further form of embodiment makes provision for the safety unit to be provided with at least one configuration parameter dataset, on the basis of which the checking for compliance with an implant-conformant limit values is undertaken.

With the aid of the at least one configuration parameter dataset the safety unit can be configured with system-specific parameters, so that the safety unit can establish correct safety-relevant variables from the safety measurement data.

The at least one configuration parameter dataset comprises for example parameters such as a gradient coil sensitivity and/or a conversion factor, on the basis of which a $B_1^+$ value can be computed from a voltage value and/or a rate of change of a magnetic field dB/dt can be computed from a current value. Usually these parameters differ depending on the design of the radio-frequency antenna unit and/or the gradient coil unit.

One possible variant of the method makes provision for the at least one configuration parameter dataset to be held at least partly in the first part. This enables a transfer of the at least one configuration parameter dataset from the second part with possibly less high safety requirements into the first part to be avoided. This makes possible a simple architecture of the safety concept, since e.g. right from the start no requirements in accordance with the safety class C have to be transmitted to the second part and/or the second part is not affected by such requirements.

For example the at least one configuration parameter dataset can be defined from the outset such that it is valid for a plurality of possible configurations of magnetic resonance apparatuses, so that ideally no device-specific configuration of the safety unit is necessary. The plurality of possible configurations of magnetic resonance apparatuses, in particular in relation to the radio-frequency antenna unit and/or the gradient coil unit, can for example involve all possible configurations of magnetic resonance apparatuses of a manufacturer, which in particular are intended for operation taking into account a person fitted with an implant. The plurality of the possible configurations can for example be a result of low-cost systems mostly being embodied differently from high-end systems.

In particular in such cases the at least one configuration parameter dataset can be based on a worst case. This is therefore advantageous in particular, since any components of the magnetic resonance apparatuses, such as for example the radio-frequency antenna unit and/or the gradient coil unit, are often not equipped with a hardware identification unit and will therefore be configured in a conventional way as a rule via software within the framework of installation and/or commissioning of the magnetic resonance apparatus. In order to avoid the otherwise necessarily high outlay for design of the software in accordance with a high safety class, e.g. safety class C, it is proposed that the configuration parameter dataset be designed as a worst-case dataset in the sense of the FPO limits. This is especially efficient, since no device-specific installation of the first part and/or of the safety unit is thus necessary.

As an alternative the at least one configuration parameter dataset can be held for a specific configuration of a magnetic resonance apparatus in the first part, so that in particular no worst case has to be considered over a plurality of possible configurations of magnetic resonance apparatuses. It is precisely when the plurality of possible configurations of magnetic resonance apparatuses would exhibit a large variance that this could possibly lead to a loss of performance.

This device-specific at least one configuration parameter dataset can for example be stored in a possibly non-volatile memory, e.g. an EEPROM, of the first part, in particular as firmware. The at least one configuration parameter dataset can be generated and/or stored within the framework of the manufacturing of the magnetic resonance apparatus.

Moreover it is conceivable for the at least one configuration parameter dataset to comprise a number of configuration parameter datasets, wherein one configuration parameter dataset will be selected from the number of configuration parameter datasets as a function of parameters of the magnetic resonance apparatus, such as e.g. characteristics of particular gradient coils and/or other components of the magnetic resonance apparatus. In order to avoid an interaction between the first part and the second part, both the number of configuration parameter datasets and also the parameters of the magnetic resonance apparatus are stored in the first part.

This advantageously enables an adapted configuration parameter dataset, preferably ideal for the respective version of the magnetic resonance apparatus, to be provided without an interaction between the first and the second part being necessary.

A further form of embodiment makes provision for the at least one configuration parameter dataset to be transmitted at least partly from the second part into the first part. This makes possible an external configuration of the safety unit. Advantageously the configuration parameter dataset is tailored to the specific type of the magnetic resonance apparatus. This makes possible an optimum adaptation of the safety apparatus and/or of the checking by the safety apparatus to the embodiment of the magnetic resonance apparatus.

The transmission can in particular take place at runtime, in particular after the safety unit has been started. In this case for example a number of configuration parameter datasets can be transmitted by program means in accordance with safety class A and/or B, wherein a configuration parameter set in accordance with safety class C will be selected from the number of configuration parameter datasets, e.g. by manual installation and/or verification by at least two operators and/or program means.

Preferably the at least one configuration parameter dataset provided will be verified on the basis of a checksum. The checksum can comprise a required checksum, which can be formed on the basis of a required device ID and the at least one configuration parameter set. Preferably in this case the required device ID is embodied, to identify a type of a magnetic resonance apparatus and/or relevant components of a magnetic resonance apparatus uniquely. The required device ID is preferably inseparably linked with a type of a magnetic resonance apparatus and/or relevant components and/or able to be established independently.

Forms of embodiment of magnetic resonance apparatuses and/or relevant, in particular field-creating, components of a magnetic resonance apparatus can in particular be subsumed here under a type, which in respect of the creation of gradient fields and/or radio-frequency fields have the same characteristics, in particular create comparable fields. A magnetic resonance apparatus and/or relevant components of a magnetic resonance apparatus of a same type do not therefore have to be of identical construction. For example it is conceivable for two magnetic resonance apparatuses of a same type in the sense described above to differ in that they have different patient support apparatuses and/or user interfaces.

On the basis of the configuration parameter dataset and/or the required checksum and/or the required device ID a self-contained data set can be created. Preferably the configuration parameter dataset and/or the self-contained dataset are stored in the second part of the magnetic resonance apparatus. The configuration parameter dataset and/or the self-contained dataset can be transmitted from the second part into the first part.

Preferably the verification of the at least one configuration parameter dataset provided and/or of the self-contained dataset takes place in the first part. In this case an actual device ID will preferably be used, which is embodied uniquely to identify the magnetic resonance apparatus actually being used and/or relevant components of the magnetic resonance apparatus actually being used. The magnetic resonance apparatus actually being used is thus the magnetic resonance apparatus with which the method will be carried out.

The actual device ID will preferably be acquired by the first part. For example the first part reads identification data from a memory, e.g. from an EEPROM, of the magnetic resonance apparatus actually being used and/or relevant components of the magnetic resonance apparatus actually being used. Another possibility consists of the actual device ID being stored in a memory of the safety unit during the manufacturing and/or installation of the magnetic resonance apparatus, from which the actual device ID can be read out. In other words the information about the system type is preferably not established by the second part, in particular the second part does not actively parameterize the first part.

An actual checksum will preferably be formed on the basis of the actual device ID and the at least one configuration parameter dataset, which can be compared with the required checksum. Where actual checksum and required checksum are equal, it can be assumed that there is no error present and the transmitted configuration parameter dataset can be used without any danger, since it is thus insured as a rule that the transmitted configuration parameter dataset exactly matches the actual state of the magnetic resonance system. Thus an end-to-end encryption of the at least one configuration parameter dataset is present here.

Through the verification of the at least one configuration parameter dataset it can be insured that no data transmission errors are present and/or that a correct configuration parameter dataset and/or self-contained dataset is present. This variant of the proposed method makes possible an efficient safety architecture. In particular the end-to-end encryption allows a plurality of storage and/or transmission options to be used.

A further form of embodiment of the method makes provision for the safety unit to check whether an operating error, in particular a software error and/or a hardware error and/or an energy supply error, is present.

A software error can comprise a crash of a program and/or an application for example. A hardware error can comprise a defect of a hardware module for example, such as e.g. a processor. An energy supply error is present for example, when a power supply to the safety unit is interrupted.

Where an operating error is present, a safe shutdown of the magnetic resonance apparatus can preferably be carried out in order to avoid unsafe operation.

A further form of embodiment of the method makes provision for a function test to be carried out in safe operating mode by the safety unit. The function test will preferably be carried out in suitable time windows, such as e.g. at each new start of the safety unit.

Preferably the function test will be carried out in a safe operating mode by the safety unit. As well as the restricted and the unrestricted operating mode, said unit represents a further operating mode, which preferably has lower limit values than the restricted operating mode and/or the unrestricted operating mode.

Preferably the safety unit will always be powered up in the safe operating mode. Preferably the operating mode only changes from the safe operating mode into the restricted operating mode when the function test is successfully concluded. If the function test has not been successfully carried out entirely or in part, the magnetic resonance apparatus will continue to be operated in safe operating mode in order to exclude any possible dangers.

Furthermore a safety unit is proposed, which is embodied to carry out a method for operating a magnetic resonance apparatus, taking into account a person fitted with an implant. The safety unit can in particular comprise one or more processors and/or one or more memory modules.

In addition a safety system is proposed, which comprises a safety unit, a switching unit and a display unit, wherein the safety system is embodied to carry out a method for operating a magnetic resonance apparatus taking into account a person fitted with an implant.

The switching unit can comprise one or more switches and/or pushbuttons. Switching information can be transferred to the safety unit with the switching unit for example, on the basis of which the safety unit sets an operating mode. The display unit can display the operating mode set, so that for example an operator can obtain information about it quickly and easily.

Furthermore a magnetic resonance apparatus with a first part and a second part is proposed. In this apparatus the first part comprises a safety unit and/or a safety system, wherein the first part is embodied to be operated separately from the second system. A separation of the parts makes possible in particular an efficient safety architecture of the magnetic resonance apparatus.

In particular the first part comprises program means in accordance with a first safety category and the second part comprises program means in accordance with a second safety category, wherein the first safety category has higher safety requirements than the second safety category.

The advantages of the inventive safety unit, of the inventive safety system and of the inventive magnetic resonance apparatus essentially correspond to the advantages of the inventive method for operating a magnetic resonance apparatus, taking into account a person fitted with an implant, which have been described in detail above. Features, advantages or alternate forms of embodiment mentioned here can likewise also be transferred to the other claimed subject matter and vice versa.

BRIEF DESCRIPTION OF THE DRAWINGS

Elements that correspond to one another are provided with the same reference characters in all figures.

DETAILED DESCRIPTION

Figure 1:
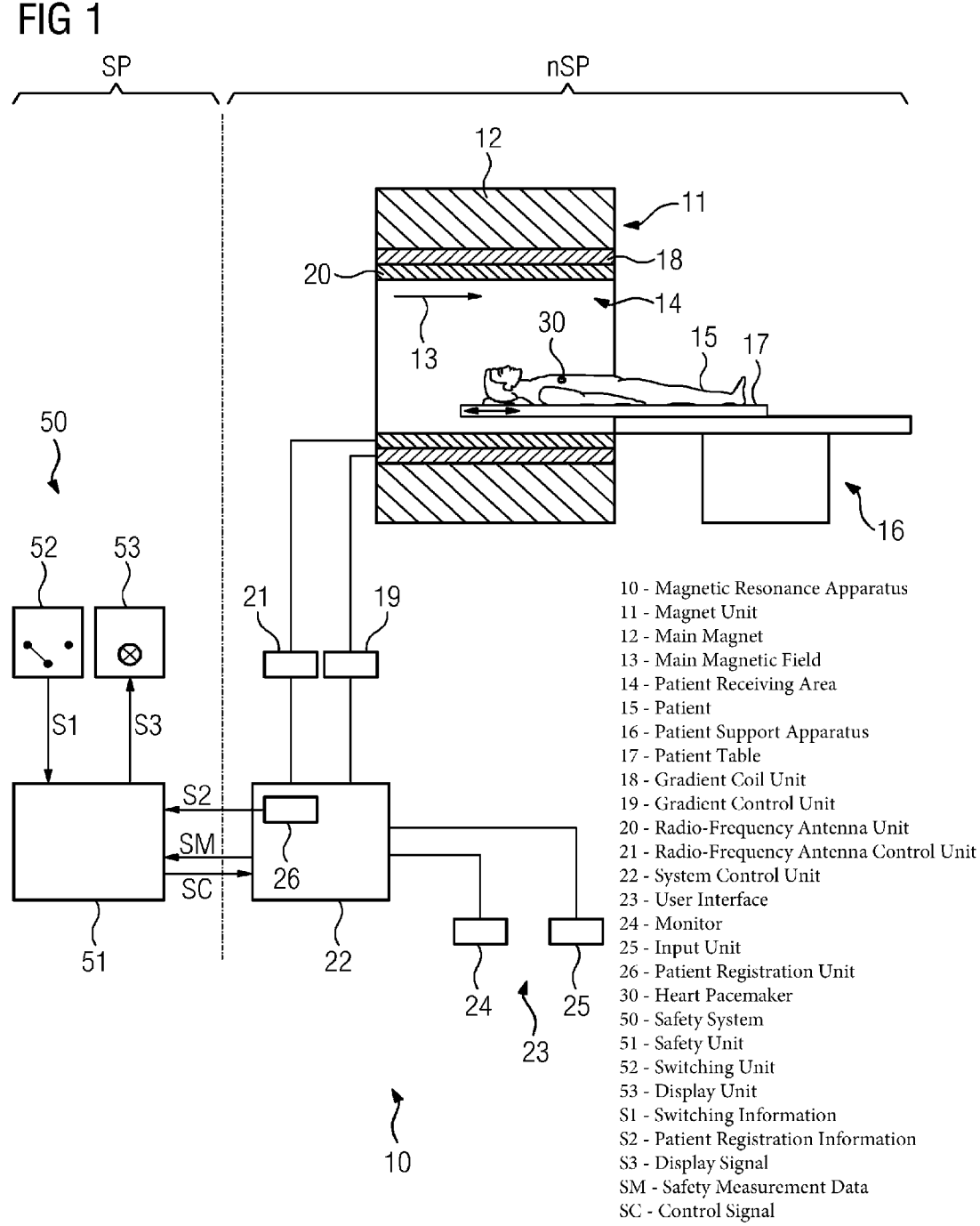
FIG. 1 shows an embodiment of a magnetic resonance apparatus with a safety system in a schematic diagram.

FIG. 1 shows one embodiment of a magnetic resonance apparatus 10 in a schematic diagram. The magnetic resonance apparatus 10 includes a magnet unit 11 that has a main magnet 12 (e.g., a superconducting main magnet) for creating a strong and, for example, temporally constant main magnetic field 13. In addition, the magnetic resonance apparatus 10 has a patient receiving area 14 for receiving a patient 15. The patient may be a person fitted with an implant, so that for, example, a heart pacemaker 30 is located in the body of the person. The patient receiving area 14 in the present exemplary embodiment is embodied cylindrically and is surrounded in a circumferential direction by the magnet unit 11 in a cylindrical shape. However, an embodiment of the patient receiving area 14 differing therefrom may be provided. The patient 15 may be pushed by a patient support apparatus 16 of the magnetic resonance apparatus 10 into the patient receiving area 14. The patient support apparatus 16 has a patient table 17 embodied so that the patient table 17 may be moved within the patient receiving area 14.

The magnet unit 11 further has a gradient coil unit 18 for creating gradient fields, which will be used for local encoding during imaging. The gradient coil unit 18 is controlled by a gradient control unit 19 of the magnetic resonance apparatus 10. The magnet unit 11 also includes a radio-frequency antenna unit 20 that in the present exemplary embodiment is embodied as a body coil permanently integrated into the magnetic resonance apparatus 10. The radio-frequency antenna unit 20 is configured for excitation of atomic nuclei, which occurs in the main magnetic field 13 created by the main magnet 12. The radio-frequency antenna unit 20 is controlled by a radio-frequency antenna control unit 21 of the magnetic resonance apparatus 10 and creates radio-frequency fields in an examination space, which is essentially formed by a patient receiving area 14 of the magnetic resonance apparatus 10. The radio-frequency antenna unit 20 is further embodied for receiving magnetic resonance signals.

For control of the main magnet 12, the gradient control unit 19 and for control of the radio-frequency control unit 21, the magnetic resonance apparatus 10 has a system control unit 22. The system control unit 22 centrally controls the magnetic resonance apparatus 10 (e.g., the carrying out of a predetermined imaging gradient echo sequence). In addition, the system control unit 22 has an evaluation unit not shown in any greater detail for evaluating medical imaging data, which will be acquired during the magnetic resonance examination. The magnetic resonance apparatus 10 has a user interface 23 that is connected to the system control unit 22. Control information, such as, for example, imaging parameters, as well as reconstructed magnetic resonance images may be displayed on a monitor 24 of the user interface 23 for a medical operator. The user interface 23 has an input unit 25, by which information and/or parameters may be entered during a measurement process by the medical operator. The system control unit also has a patient registration unit 26.

The previously explained components of the magnetic resonance apparatus 10 will be included in a second part nSP, while a first part SP of the magnetic resonance apparatus 10 includes a safety system 50 that has a safety unit 51, a switching unit 52, and a display unit 53. The safety unit 51 is connected to the system control unit 22 and is embodied, during an examination of a person fitted with an implant, for example, to check the magnetic resonance apparatus 10 in a restricted operating mode for compliance with implant-conformant limit values.

The first part SP of the magnetic resonance apparatus fulfills higher safety requirements than the second part nSP. This provides that checking for compliance with implant-conformant limit values is advantageously done especially safely. For example, the first part SP (e.g., exclusively) may have program means (e.g., a program) in accordance with a first safety category, and the second part nSP may have program means (e.g., a program) in accordance with a second safety category. The first safety category has higher safety requirements than the second safety category. The first part SP may be operated separately from the second part nSP, so that no safety-critical interaction by the second part nSP with the first part SP is possible.

The implant-conformant limit values will be predetermined by a standard, for example, such as Standard IEC 60601-2-33. In this standard, an operating mode in accordance with FPO:B is specified, which makes provision that, for example, for the values $B_1{}^+_{peak}$, $B_1{}^+_{rms}$, $(|dB/dt|_{peak})_{FPO}$ and $(|dB/dt|_{rms})_{FPO}$ certain limit values are to be complied with. Peak values, such as, for example, $B_1{}^+_{peak}$ and/or $(|dB/dt|_{peak})_{FPO}$, may be permanently monitored. Effective values, such as, for example, $B_1{}^+_{rms}$ and/or $(|dB/dt|_{rms})_{FPO}$ may be averaged over a first interval of, for example, 10 seconds and/or are checked in a cycle of a second interval of, for example, 1 second. This is intended to provide that there will be no danger for the patient from a magnetic resonance examination of patients who are fitted with an implant in accordance with FPO:B. The restricted operating in this case advantageously allows only one operation of the magnetic resonance apparatus, provided the limit values in accordance with FPO:B will be complied with.

To check for compliance with implant-conformant limit values, the safety unit will be provided during the examination with safety measurement data SM, such as, for example, data about wideband and/or narrowband radio-frequency excitation of the radio-frequency antenna unit 20 and/or data about gradient currents of the gradient coil unit 18. In one embodiment, this data is partly verified in order to provide that the data has been correctly acquired and transmitted. Various mechanisms such as, for example, a redundant measurement data flow that, depending on risk of failure and/or falsification, will be checked permanently or cyclically against one another may be provided for this.

Should it be established that one or more implant-conformant limit values have been exceeded, the safety unit 51 transfers a control signal SC to the system control unit 22, which leads to a safe shutdown of the magnetic resonance apparatus 10.

In addition, the safety unit 51 checks whether an operating error is present. If this is the case, the safety unit 51 sends a control signal SC to the system control unit 22, through which a safe shutdown of the magnetic resonance apparatus 10 will be initiated. Such an operating error may, for example, be a software error and/or a hardware error and/or an energy supply error.

The switching unit 52 is embodied to transfer switching information S1 to the safety unit 51. The switching unit 52 may, for example, be embodied as a mechanical switch or mechanical pushbutton. However, the switching unit 52 may be implemented in the form of an electronic user interface, in which the switch is operated via an input device, such as, for example, a computer mouse and/or a keyboard. The input device may be an apparatus independent of the user interface 23 in order to avoid any intermeshing of the first part SP and second part nSP. However, the switching unit 52 may be controlled from the second part nSP, for example, from the user interface 23. In this case, external measures may be taken, such as, for example, a check of the operating mode by the operating personnel, in order to provide a sufficient safety (e.g., in accordance with safety class A).

With the aid of the switching unit 52, operating personnel may set whether operation of the magnetic resonance apparatus 10 in restricted operating mode (e.g., in accordance with FPO:B) is desired or not. In the first case (e.g., if the restricted operating mode is to be active), the safety unit 51 will be provided with active switching information S1. If the restricted operating mode is not to be active, but instead of this, for example, an unrestricted operating mode, the safety unit 51 will be provided with passive switching information S1.

If there is a change of patient, the patient registration unit 26 passes on patient registration information S2 to the safety unit 51 and causes the safety unit 51 to evaluate the switching information S1. Based on the information provided (e.g., the patient registration information S2 and the switching information S1), the safety unit 51 thus sets a specific operating state. In addition, the operating state set will be displayed by the display unit 53 (e.g., a light emitting diode (LED)). For this purpose, a display signal S3 will be transmitted from the safety unit 51 to the display unit 53. The operating personnel may thus check whether the display corresponds to the patient (e.g., a green LED display for a patient having an implant and a red LED display for a patient free from implants).

Figure 2:
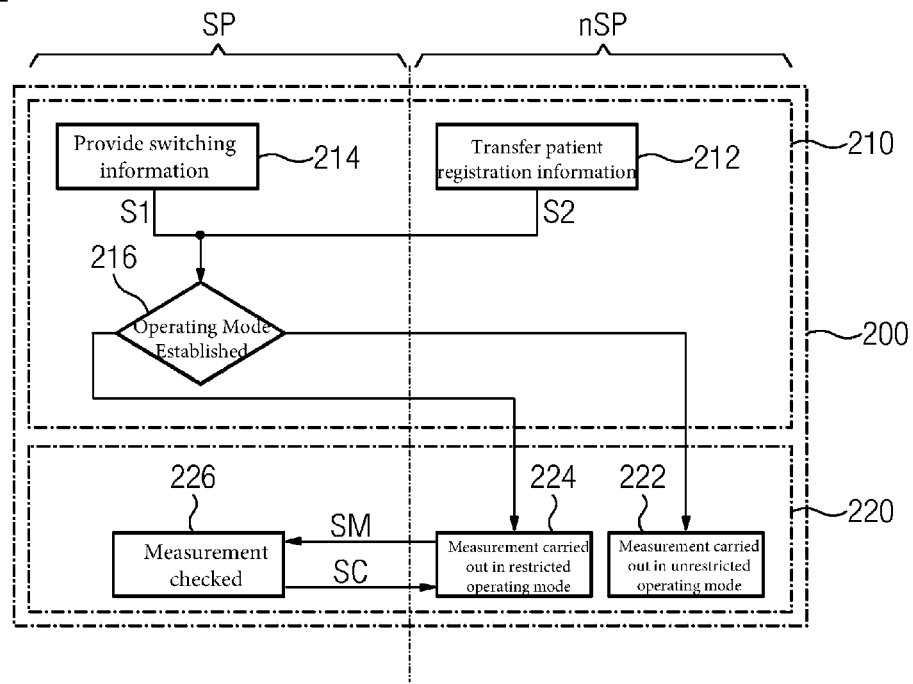
FIG. 2 shows a block diagram of a form of embodiment of a method.

FIG. 2 shows a scheme of an embodiment of a method for operating the magnetic resonance apparatus 10, taking into account a person fitted with an implant, using the safety unit 51. In this scheme, a measurement 200 includes preparing for a measurement 210 and carrying out a measurement 220. In act 214 of preparing for the measurement 210, switching information S1 is provided by the switching unit 52 to the safety unit 51. Switching unit 52 and safety unit 51 are elements of the first part SP of the magnetic resonance apparatus 10, so that this part of the method also takes place in the first part SP.

In act 212, patient registration information S2 will be transferred from the second part nSP from the patient registration unit 26 to the safety unit 51. This is advantageously done when there is an impending measurement to be carried out on a new patient 15. In response to this message and/or trigger, in act 216, an operating mode is established, which is to be applied in the carrying out of the measurement 200. If a restricted operating mode is established, in act 224, the measurement is consequently carried out in the restricted operating mode. In this mode, in act 226, the measurement will be checked by the safety unit 51. To this end, safety measurement data SM is transmitted to the safety unit 51.

With the aid of control signals SC, the safety unit 51 may influence the measurement 224 in the restricted operating mode (e.g., abort it if an implant-conformant limit value is exceeded). If an unrestricted operating mode is established in act 216, the measurement is consequently carried out in act 222 in the unrestricted operating mode without checking by the safety unit 51.

Figure 3:
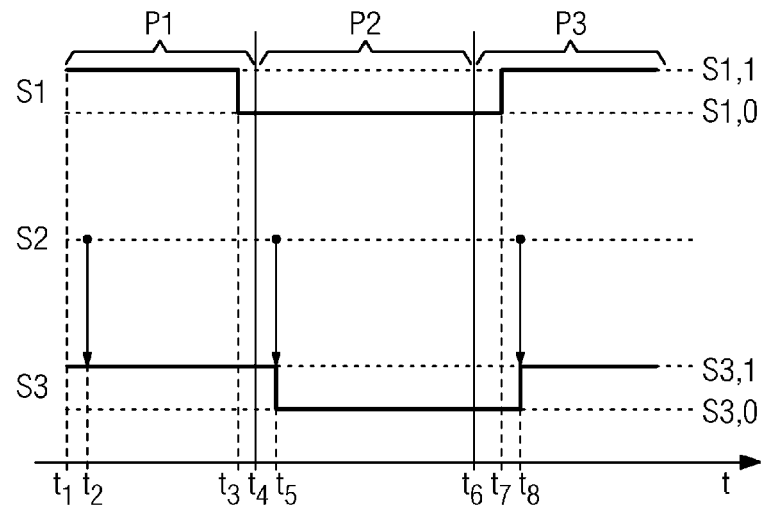
FIG. 3 shows an exemplary execution sequence of setting an operating mode in accordance with a first variant of the method.

FIGS. 3 to 6 illustrate the establishing and resulting setting of the operating mode in act 216 in greater detail. Thus, FIG. 3 shows a curve over time t in accordance with a first variant of the method. The safety unit 51 receives switching information S1 (e.g., in the form of a signal such as an electronic and/or electrical signal) from a number of possible items of switching information. In this case, two items of switching information are possible here (e.g., active switching information S1,1 and passive switching information S1,0). These two items of switching information correspond, for example, to two switching states of the switching unit 52, which are able to be set by the operating personnel.

The safety unit 51 receives patient registration information S2 at different times $t_2$, $t_5$, $t_8$ from the patient registration unit 26 (e.g., in the form of a signal such as an electronic and/or electrical signal), which serves as a trigger for the evaluation of the switching information. Depending on the switching information S1 provided and on the patient registration information S2 provided, the safety unit 51 sets an operating mode from a number of possible operating modes. The operating mode set will be displayed by the display unit 53 (e.g., by switching on a light-emitting diode), so that a specific operating mode corresponds to a specific display signal S3. Two possible operating modes are shown (e.g., the restricted operating mode S3,1 and the unrestricted operating mode S3,0).

Figure 4:
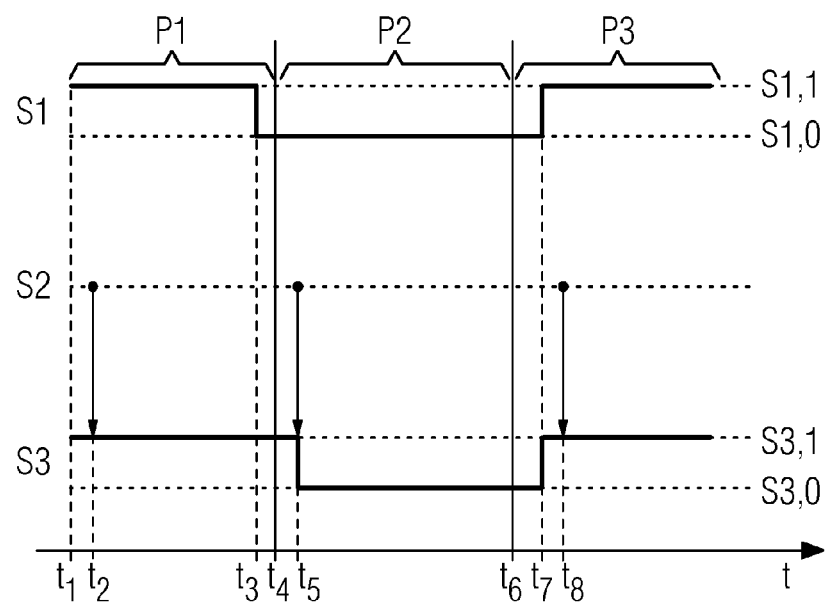
FIG. 4 shows an exemplary execution sequence of setting an operating mode in accordance with a second variant of the method.

In the examples shown in FIGS. 3 and 4, three patients P1, P2, P3 are examined with the aid of the magnetic resonance apparatus 10, where patients P1 and P3 are persons fitted with an implant. For the examination of the first patient P1, a first period of time between the times $t_1$ and $t_4$ is provided, for the examination of the second patient P2, a second period of time between the times $t_4$ and $t_6$ is provided, and the third patient P3 is to be examined after the time $t_6$.

The initial operating mode is the restricted operating mode S3,1. At time $t_1$, the switching state is changed from S1,0 to S1,1. This is done, for example, by the operating personnel of the magnetic resonance apparatus 10 in the knowledge that there is now to be an examination of a person fitted with an implant. During the further course of the examination (e.g., during the preparation phase), in which there is a registration of the patient P1, at time $t_2$, the patient registration unit 52 sends patient registration information S2 to the safety unit 51. The switching information S1 will subsequently be evaluated, so that the operating mode subsequently continues to remain in the restricted operating mode S3,1. At this point in time, the active switching information S1,1 will be provided.

At time $t_3$, the switching state of the switching unit will be changed to S1,0, for example, because the recording of the magnetic resonance data has been ended, the first patient P1 is no longer located in the patient receiving area 14, and the operating personnel assume that the next patient is not a person fitted with an implant. At time $t_3$, however, the operating state S3 will not (yet) be changed. Only when, at time $t_5$, patient registration information S2 will be received by the safety unit 51 for the second patient P2 will there be a change of the operating mode. The unrestricted operating mode S3,0 will thus only be set when, at the time of the provision of the patient registration information S2, the switching information S1 provided is the passive switching information S1,0.

A provision of patient registration information S2 on its own does not trigger any deactivation of the restricted operating state, but this only occurs when at the same time the current switching information S1 is passive switching information S1,0. Therefore, the provision of the patient registration information S2 is not safety-critical.

At time $t_7$, active switching information S1,1 will be set. In accordance with the variant shown in FIG. 3 this switching information will only be evaluated at time $t_8$, triggered by patient registration information S2. The evaluation results in a change into the restricted operating mode S3,1.

By contrast, in accordance with the variant shown in FIG. 4, the change into the restricted operating mode S3,1 already occurs at time $t_7$ concurrently with the change of the switching information from S1,0 to S1,1. An activation of the restricted operating mode S3,1 thus does not require any triggering by patient registration information S2.

The generation and/or transfer of the switching information S1 and/or the display signal S3 may be implemented as a hardware solution, so that this will be carried out safely and, for example, fulfills the safety classes C of Standard IEC 62304.

The proposed safety concept allows the patient registration information S2 to be generated by software in accordance with safety class B. If an error occurs during this process, so that the safety unit 51 will not be provided with any patient information S2, the following cases are, for example, able to be identified.

A) If the restricted operating mode S3,1 is in effect and the passive switching information S1,0 will be set, then the magnetic resonance apparatus 10 continues to remain in the restricted operating mode S3,1 for as long as no patient information S2 is provided. If necessary, the operating personnel recognizes the malfunction by the display unit 53 and repeats the registration until such time as the desired unrestricted operating mode S3,0 will be activated and displayed.

B) If the unrestricted operating mode S3,0 is in effect and the active switching information S1,1 will be set, two variants may be identified. In accordance with FIG. 3, the magnetic resonance apparatus 10 continues to remain in the unrestricted operating mode S3,0 for as long as no patient information S2 is provided. If necessary, the operating personnel recognizes the malfunction using the display unit 53 and repeats the registration until such time as the desired restricted operating mode S3,1 will be activated and displayed. In accordance with FIG. 4, the restricted operating mode S3,1 will be activated immediately, as soon as the active switching information S1,1 is set.

The display state and/or the operating mode S3 at a point in time t as a function of the switching information S1 and of the patient registration information S2 at point in time t, as well as of the operating mode S3 at an earlier point in time t−1, may be described with the following logical equation, which is valid at point in time $t_2$, $t_5$, $t_8$ of the provision of the patient information S2:

$$S3(t) = (S1(t) \vee S3(t-1)) \wedge \overline{(\overline{S1(t)} \wedge S2(t))}$$

Figure 5:
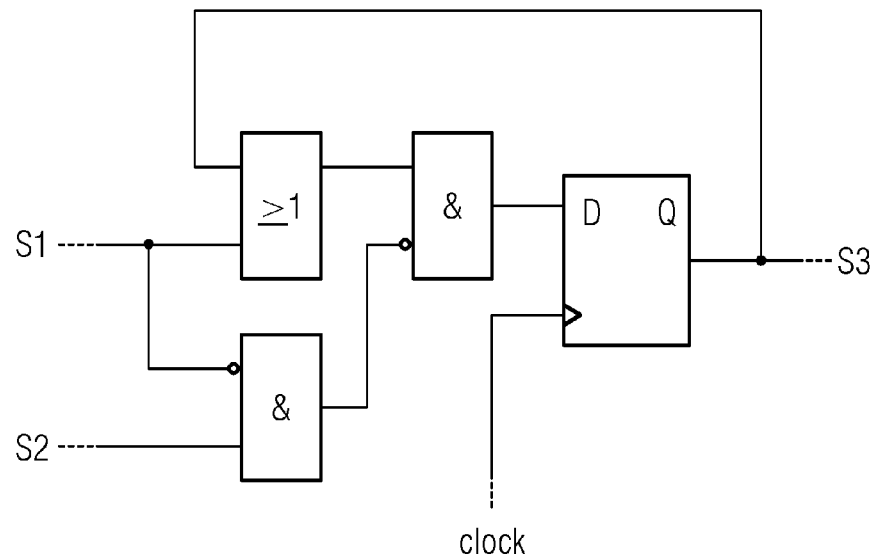
FIG. 5 shows a diagram of a possible setting of an operating mode with discrete logic elements.

This equation may be implemented in the safety unit 51, for example, using a software program and/or a discrete logic by using a circuit, as is shown in FIG. 5.

With this design, a deactivation of the restricted operating mode S3,1 is controlled solely by the switching unit 52 and the safety unit 51, which as elements of the first part SR are relevant to safety. The provision of the patient registration information S2 serves as a trigger, when the switching information S1 is to be evaluated, but does not deactivate the restricted operating mode S3,1 itself.

Figure 6:
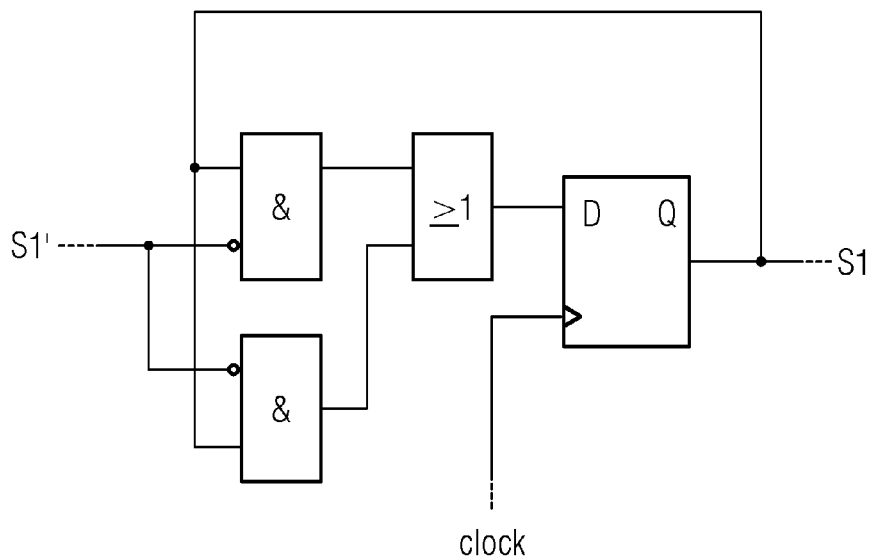
FIG. 6 shows a diagram of a possible evaluation of switching information with discrete logic elements.

FIG. 6 shows a variant of this configuration, which uses a pushbutton instead of a switch. This has the advantage that only the display unit displays the current operating mode and the operating personnel will not possibly be misled by a visible mechanical switch position of a switch. The pushbutton creates a signal S1' that switches over the state of a latch register, where the output of this latch register will be used as switching information S1. With the following equation, which is valid at point in time $t_2$, $t_5$, $t_8$ of the provision of the patient information S2, a description may be provided as for the above equation as well as for FIG. 3 with:

$$S3(t)=(\overline{S1'(t)} \wedge S1(t-1)) \vee (S1'(t) \wedge \overline{S1(k-1)})$$

Checking for compliance with implant-conformant limit values in act 226 has already been explained with reference to FIG. 2. For this purpose, the safety unit 51 may be provided with at least one configuration parameter dataset as well as the safety measurement data SM already mentioned, which for example, includes information about a sensitivity of gradient pulses and/or scaling factors, such as, for example, strength of a resulting $B_1^+$ field per volt of an applied voltage. With the aid of such information, an evaluation of the safety measurement data SM may be made easier.

Figure 7:
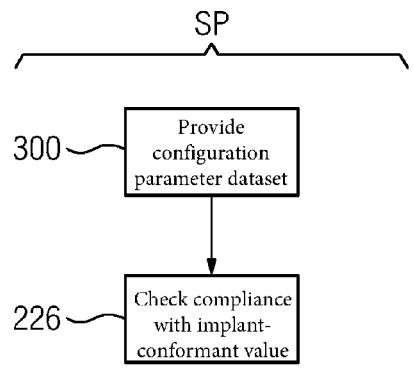
FIG. 7 shows a block diagram of a first form of an embodiment of a part method for provision of at least one configuration parameter set.

FIG. 7 shows a possible form of embodiment for provision of the at least one configuration parameter set, based on which, in act 226, the checking for compliance with the implant-conformant limit values is done. In this case, the at least one configuration parameter dataset is held in the first part SP and will be provided in act 300. This enables a transmission of the at least one configuration parameter set from outside the first part SP to be avoided.

In this case, a fixed configuration parameter dataset may be used, which is stored, for example, within the safety unit 51. In accordance with a possible variant, the fixed configuration parameter dataset is embodied such that the fixed configuration parameter dataset conservatively forms an envelope covering a plurality of gradient coils units and/or radio-frequency antenna units, for which the safety unit 51 is to be applicable. Although this enables a single safety unit 51 to be used in a plurality of differently embodied magnetic resonance apparatuses, the maximum possible performance of the magnetic resonance apparatuses may not possibly be exploited by this.

In accordance with a variant not shown in any greater detail here, the at least one configuration parameter dataset includes a number of configuration parameter datasets, where one configuration parameter dataset dependent on parameters of the magnetic resonance apparatus 10 will be selected from the number of configuration parameter datasets. Two possibilities may, for example, be identified: A) The configuration parameter dataset valid for the system type will be permanently set during manufacturing and/or installation by, for example, a number of persons (e.g., four-eyes principle); B) The system type will be recognized, for example, automatically using a hardware recognition and transferred to the safety unit 51.

Figure 8:
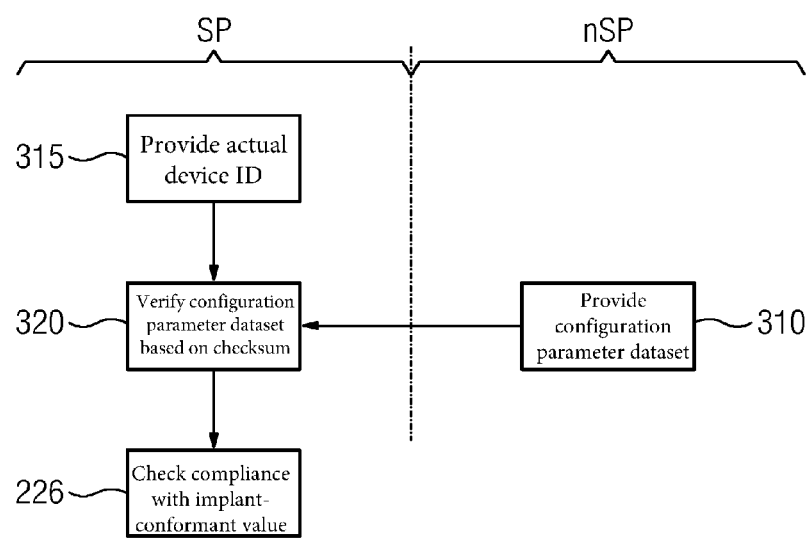
FIG. 8 shows a block diagram of a second form of embodiment of a part method for provision of at least one configuration parameter set.

FIG. 8 shows a further possibility for provision of the at least one configuration parameter dataset. In act 310, a configuration parameter dataset of the safety unit 51 held in the second part nSP will be provided, which will be verified in act 320 based on a checksum. In act 315, an actual device ID 408 will be provided, which will be established by the first part SP, for example, by hardware recognition and/or will be read by program means (e.g., a program) of the safety unit 51 to be read out from a memory of the first part SP, in which the actual device ID will be stored (e.g., within the framework of the manufacturing and/or installation of the magnetic resonance apparatus 10). Provided the verification is successful, in act 226, the checking for compliance with the implant-conformant limit values using the configuration parameter dataset is undertaken.

Figure 9:
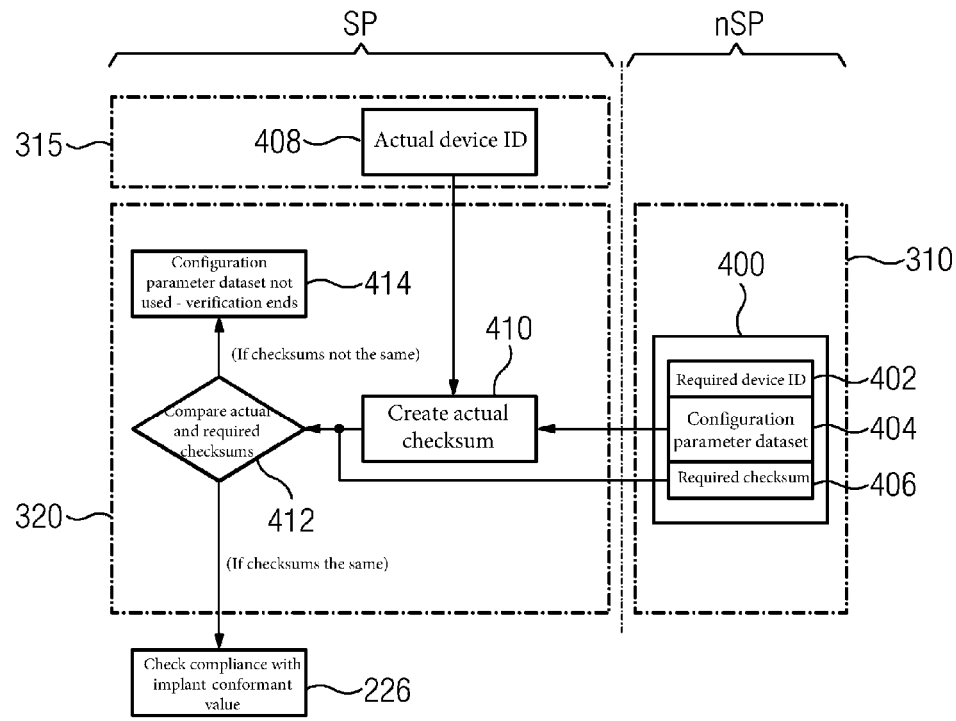
FIG. 9 shows a detailed block diagram of a variant of the second part method for provision of at least one configuration parameter set.

A more detailed form of embodiment will be shown by FIG. 9. In act 310, a self-contained dataset 400 will be provided, which includes a required device ID 402, a configuration parameter dataset 404, and a required checksum 406.

The actual device ID may be embodied uniquely to identify the magnetic resonance apparatus 10 actually used and/or relevant components of the magnetic resonance apparatus 10 actually used, such as, for example, the radio-frequency antenna unit 20 and/or the gradient coil unit 18.

The required checksum 406 will be created based on the required device ID 402 and the configuration parameter dataset 404. The required device ID 402 is characteristic for one type of the magnetic resonance apparatus 10 and/or for relevant components of the magnetic resonance apparatus 10, such as, for example, a type of the radio-frequency antenna unit 20 and/or a type of the gradient coil unit 18.

In act 410, an actual checksum will be created in the first part SP based on the actual device ID and the configuration parameter dataset 404, which will be compared in act 412 with the required checksum 406. If the result of this checking is that the actual checksum and the required checksum 406 are the same, then in act 226, the checking for compliance with the implant-conformant limit values using the configuration parameter dataset 404 is undertaken. Otherwise, the configuration parameter dataset 404 will not be used, and the verification of the configuration parameter dataset 404 ends in act 414.

The self-contained dataset 400 may be created, for example, within the framework of the development and/or manufacturing of the magnetic resonance apparatus 10 and be stored outside the first unit (e.g., in the system control unit 22) and/or together with other parameterizations of the magnetic resonance apparatus. The end-to-end encryption shown here allows recourse to conventional storage and transmission techniques, the development of which is often subject to less severe restrictions.

Figure 10:
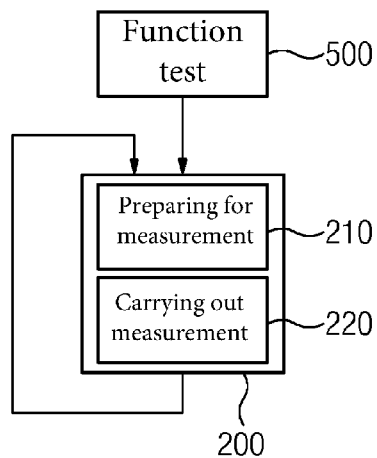
FIG. 10 shows a block diagram of a form of embodiment of a method with a function test.

FIG. 10 shows an expanded method, with a function test in act 500. The function test may be carried out in a safe operating mode by the safety unit 51. The safe operating mode may have lower limit values than the restricted operating mode and/or the unrestricted operating mode. The operating mode only changes from the safe operating mode into the restricted operating mode when the function test is successfully concluded.

Act 500 will be carried out at specific time intervals (e.g., every hour, every day or every week) and/or in suitable time windows, such as, for example, on each new start of the safety unit. The function test thus does not have to be carried out before each examination, but a number of measurements 200 may be carried out between two function tests.

The method described in detail above as well as the acquisition pattern creation unit and magnetic resonance apparatus merely involve exemplary embodiments, which may be modified by the person skilled in the art in a very wide variety of ways, without departing from the field of the invention. The use of the indefinite article "a" or "an" does not exclude the features concerned also being able to be present more than once. The terms "unit" and "module" do not exclude the components concerned consisting of a number of interacting part-components, which if necessary, may also be spatially distributed.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for operating a magnetic resonance apparatus using a safety unit, taking into account persons fitted with implants, wherein the magnetic resonance apparatus comprises a first part and a second part, wherein the first part is operated separately from the second part and comprises the safety unit, the method comprising:
   controlling, by the safety unit during an examination of a person fitted with an implant, the magnetic resonance apparatus in a restricted operating mode to comply with implant-conformant limit values,
   wherein the first part comprises a switching unit,
   wherein the safety unit is provided with switching information from a number of possible items of switching information by the switching unit, and
   wherein an operating mode is set by the safety unit from a number of possible operating modes, depending on the switching information provided.

2. The method of claim 1, wherein the first part fulfills higher safety requirements than the second part.

3. The method of claim 1, wherein the first part is operated with a program in accordance with a first safety category,
   wherein the second part is operated with a program in accordance with a second safety category, and
   wherein the first safety category has higher safety requirements than the second safety category.

4. The method of claim 1, wherein the switching unit comprises a switch, a pushbutton, or the switch and the pushbutton.

5. The method of claim 1, wherein the second part comprises a patient registration unit,
   wherein the safety unit is provided with patient registration information by the patient registration unit, and
   wherein a change of operating mode is initiated at least partly by the patient registration information provided.

6. The method of claim 5, wherein the number of possible operating modes comprises an unrestricted operating mode and the restricted operating mode,
   wherein the number of possible items of switching information comprises active switching information and passive switching information, and
   wherein the unrestricted operating mode is set when, at the time the patient registration information is provided, the switching information provided is the passive switching information.

7. The method of claim 6, wherein the restricted operating mode is set when, at the time the patient registration information is provided, the switching information provided is the active switching information.

8. The method of claim 6, wherein the restricted operating mode is set when the switching information provided is the active switching information.

9. The method of claim 1, wherein the first part comprises a display unit that displays the operating mode.

10. The method of claim 1, wherein the safety unit is provided with safety measurement data during the examination, based on which a check for compliance with the implant-conformant limit values is made.

11. The method of claim 10, wherein the safety measurement data provided is at least partly verified.

12. The method of claim 1, wherein the safety unit is provided with at least one configuration parameter dataset, based on which a check for compliance with the implant-conformant limit values is made.

13. The method of claim 12, wherein the at least one configuration parameter dataset is stored at least partly in the first part.

14. The method of claim 12, wherein the at least one configuration parameter dataset comprises a number of configuration parameter datasets, and
   wherein one configuration parameter dataset is selected from the number of configuration parameter datasets depending on parameters of the magnetic resonance apparatus.

15. The method of claim 12, wherein the at least one configuration parameter dataset is transmitted at least in part from the second part into the first part.

16. The method of claim 15, wherein the at least one configuration parameter dataset provided is verified based on a checksum.

17. The method of claim 16, wherein the checksum comprises a required checksum configured to identify uniquely a type of magnetic resonance apparatus, relevant components of a magnetic resonance apparatus, or a combination thereof, and
   wherein the required checksum is created based on a required device ID and the at least one configuration parameter dataset.

18. The method of claim 17, wherein the checksum comprises an actual checksum that is configured to identify uniquely the magnetic resonance apparatus, relevant components of the magnetic resonance apparatus, or a combination thereof,
   wherein the actual checksum is created based on an actual device ID and the at least one configuration parameter dataset, and
   wherein the actual checksum is compared with the required checksum.

19. The method of claim 1, wherein the safety unit checks whether an operating error is present.

20. The method of claim 19, wherein the operating error comprises a software error, a hardware error, an energy supply error, or any combination thereof.

21. The method of claim 1, wherein a function test is carried out by the safety unit in a safe operating mode, and
   wherein the safe operating mode has lower limit values than the restricted operating mode, the unrestricted operating mode, or the restricted operating mode and the unrestricted operating mode.

22. The method of claim 21, wherein the operating mode changes from the safe operating mode into the restricted operating mode when the function test is successfully concluded.

23. A safety unit configured to operate a magnetic resonance apparatus taking into account persons fitted with implants, wherein the magnetic resonance apparatus comprises a first part and a second part, wherein the first part is operated separately from the second part and comprises the safety unit, the safety unit comprising:
a processor configured to control, during an examination of a person fitted with an implant, the magnetic resonance apparatus in a restricted operating mode to comply with implant-conformant limit values,
wherein the first part comprises a switching unit,
wherein the safety unit is provided with switching information from a number of possible items of switching information by the switching unit, and
wherein the safety unit is configured to set an operating mode from a number of possible operating modes, depending on the switching information provided.

24. A safety system comprising:
a safety unit configured to operate a magnetic resonance apparatus taking into account persons fitted with implants, wherein the magnetic resonance apparatus comprises a first part and a second part, wherein the first part is operated separately from the second part and comprises the safety unit, the safety unit comprising a processor configured to control, during an examination of a person fitted with an implant, the magnetic resonance apparatus in a restricted operating mode to comply with implant-conformant limit values;
a switching unit; and
a display unit,
wherein the switching unit is configured to transfer switching information to the safety unit,
wherein the safety unit is configured to set an operating mode based on the switching information, and
wherein the display unit is configured to display the operating mode set.

25. A magnetic resonance apparatus comprising:
a first part and a second part,
wherein the first part comprises a safety system comprising a safety unit,
wherein the safety unit is configured to operate the magnetic resonance apparatus taking into account persons fitted with implants, wherein the first part comprises the safety unit, the safety unit comprising a processor configured to control, during an examination of a person fitted with an implant, the magnetic resonance apparatus in a restricted operating mode to comply with implant-conformant limit values,
wherein the safety system comprises a switching unit that is configured to transfer switching information from a number of possible items of switching information to the safety unit, the safety unit, which is configured to set an operating mode from a number of possible operating modes based on the switching information, and a display unit configured to display the operating mode set, and
wherein the first part is configured to be operated separately from the second part.

26. The magnetic resonance apparatus of claim 25, wherein the first part comprises a program in accordance with a first safety category,
wherein the second part comprises a program in accordance with a second safety category, and
wherein the first safety category has higher safety requirements than the second safety category.

27. A method for operating a magnetic resonance apparatus using a safety unit, taking into account persons fitted with implants, wherein the magnetic resonance apparatus comprises a first part and a second part, wherein the first part is operated separately from the second part and comprises the safety unit, the method comprising:
controlling, by the safety unit during an examination of a person fitted with an implant, the magnetic resonance apparatus in a restricted operating mode to comply with implant-conformant limit values,
wherein the safety unit is provided with at least one configuration parameter dataset, based on which a check for compliance with the implant-conformant limit values is made,
wherein the at least one configuration parameter dataset is transmitted at least in part from the second part into the first part,
wherein the at least one configuration parameter dataset provided is verified based on a checksum,
wherein the checksum comprises a required checksum configured to identify uniquely a type of magnetic resonance apparatus, relevant components of a magnetic resonance apparatus, or a combination thereof, and
wherein the required checksum is created based on a required device ID and the at least one configuration parameter dataset.

28. The method of claim 27, wherein the at least one configuration parameter dataset is stored at least partly in the first part.

29. The method of claim 27, wherein the at least one configuration parameter dataset comprises a number of configuration parameter datasets, and
wherein one configuration parameter dataset is selected from the number of configuration parameter datasets depending on parameters of the magnetic resonance apparatus.

30. The method of claim 27, wherein the checksum comprises an actual checksum that is configured to identify uniquely the magnetic resonance apparatus, relevant components of the magnetic resonance apparatus, or a combination thereof,
wherein the actual checksum is created based on an actual device ID and the at least one configuration parameter dataset, and
wherein the actual checksum is compared with the required checksum.

* * * * *